United States Patent [19]

Aust et al.

[11] Patent Number: 5,468,628
[45] Date of Patent: Nov. 21, 1995

[54] COMPOUNDS AND METHODS FOR GENERATING OXYGEN AND FREE RADICALS USED IN GENERAL OXIDATION AND REDUCTION REACTIONS

[75] Inventors: Steven D. Aust; David P. Barr, both of Logan; Thomas A. Grover, Hyde Park; Manish M. Shah; Namhyun Chung, both of Logan, all of Utah

[73] Assignee: Utah State University Foundation, Logan, Utah

[21] Appl. No.: 368,555

[22] Filed: Jan. 4, 1995

Related U.S. Application Data

[63] Continuation of Ser. No. 1,106, Jan. 5, 1993, Pat. No. 5,389,356.

[51] Int. Cl.$^6$ .................................. C12P 3/00; C02F 3/02
[52] U.S. Cl. .................... 435/168; 435/132; 435/192; 435/262; 435/262.5; 435/911; 423/659
[58] Field of Search ....................................... 435/168, 192, 435/262, 262.5, 911, 132; 423/659

[56] References Cited

U.S. PATENT DOCUMENTS

| | | | |
|---|---|---|---|
| 3,888,890 | 6/1975 | Kirchner et al. | 260/369 |
| 3,923,966 | 12/1975 | Vaughan | 423/573 |
| 3,998,936 | 12/1976 | Ernst et al. | 423/588 |
| 4,102,950 | 7/1978 | Pilipovich et al. | 823/910 |
| 4,318,895 | 3/1982 | Richardson et al. | 423/579 |
| 4,533,443 | 8/1985 | Wrighton et al. | 204/84 |
| 4,554,075 | 11/1985 | Chang et al. | 210/611 |
| 4,629,690 | 12/1986 | Weng et al. | 435/7 |
| 4,751,068 | 6/1988 | Bickar et al. | 423/437 |
| 4,891,320 | 1/1990 | Aust et al. | 435/262 |
| 4,959,135 | 9/1990 | Zenner et al. | 204/129 |
| 5,143,710 | 9/1992 | Sawyer et al. | 423/581 |
| 5,389,356 | 2/1995 | Aust et al. | 423/659 |

OTHER PUBLICATIONS

Barr, David P., et al., "Production of Hydroxyl Radical by Lignin Peroxidase from Phanerochaete Chrysosporium", Archives of Biochemistry and Biophysics, vol. 298, No. 2, pp. 480–484, Nov. 1, 1992.

Barr, David P., et al., "Veratryl Alcohol–Dependent Production of Molecular Oxygen by Lignin Peroxidase", The Journal of Biological Chemistry, vol. 268, No. 5, pp. 1–4, 1993.

Popp, Janet L., et al., "Lignin Peroxidase Oxidation of $mN^2+$ in the Presence of Veratryl Alcohol, Malonic or Oxalic Acid, and Oxygen", vol. 29, pp. 10475–10480, Jun. 1990.

Shah, Manish M., et al., "Use of White Rot Rungi in the Degration of Enfironmental Chemicals", Toxicology Letters, pp. 1–9, 1992.

Shah, Manish M., et al., "On the Mechanism of Inhibition of the Veratryl Alcohol Oxidase Activity of Lignin Peroxidase H2 by EDTA", The Journal of Biological Chemistry, vol. 267, No. 30, pp. 21564–21569, Oct. 30, 1992.

Shah, Manish M., et al., "Oxidation of halides by Peroxidases and their Subsequent Reductions", Archives of Biochemistry and Biophysics, vol. 300, No. 1, pp. 001–005, 1993.

*Primary Examiner*—Herbert J. Lilling
*Attorney, Agent, or Firm*—Workman Nydegger Seeley

[57] ABSTRACT

Composition and methods; for carrying out a variety of oxidation reactions, reduction reactions, or both utilizing a free radical generating catalyst, a mediator, and a reductant are disclosed. The free radical generating catalyst is generally a peroxidase obtained from living organisms, such as white rot fungi. Suitable peroxidases include lignin peroxidase, horse radish peroxidase, and lactoperoxidase. Suitable mediators include veratryl alcohol, iodine, methoxybenzenes, Mn II, and ABTS. Suitable reductants include EDTA, oxalate, hydroquinones, quinones plus quinone reductase, and hydrogen peroxide.

14 Claims, 6 Drawing Sheets

COMPOUNDS AND METHODS FOR GENERATING OXYGEN AND FREE RADICALS USED IN GENERAL OXIDATION AND REDUCTION REACTIONS

This work was supported by a grant from the National Institute of Health, Grant No. ESO4922. This application is a continuation of application Ser. No. 08/001,106, filed Jan. 5, 1993, now U.S. Pat. No. 5,389,356.

BACKGROUND

1. Field of the Invention

This invention describes a method for catalyzing oxidation reactions, reduction reactions, or both using free radical intermediates. More specifically, this invention involves the use of biologically derived peroxidases in the generation of a variety of oxidation or reduction agents consisting of cation radicals, anion radicals, neutral radicals, or oxygen radicals. Such oxidation and reduction agents can be employed separately or in combination to carry out a wide variety of oxidation or reduction reactions, some of which involve the degradation of recalcitrant organic compounds such as organic environmental pollutants.

2. The Relevant Technology

The use of oxidation or reducing agents to carry out oxidations or reductions on targeted substrates is mature technology well-known in the art. Desired oxidation and reduction reactions can be carried out on a multitude of different substrates simply by reacting the substrate with a stoichiometrically adequate amount of an appropriate oxidant or reductant. Commonly used oxidants or reductants which can be produced in a commercially feasible manner include a wide variety of generally inorganic agents. The feasibility of using such oxidants or reductants is often limited by such restraints as the cost of the reactant in relation to the value of the reacted substrate, the ability to control the reaction, and the ability to obtain suitable concentrations of the reacted substrate in reasonably pure amounts.

More complicated oxidation and/or reduction reactions have been created which involve organic intermediates, such as hydroquinones, alkylanthraquinones, anilines, hydrazines, or metal complexed chelating agents. In some cases, the reactant is a catalyst which is continuously regenerated. For example, U.S. Pat. No. 5,143,710 to Sawyer et al. discloses methods for generating superoxide ions in situ catalyzed by aniline, N-substituted aniline compounds, or phenylhydrazine compounds. The superoxide ion, which is an anion radical, is useful for a number of different applications discussed within Sawyer et al. Superoxide ions have proven particularly effective in destroying a variety of halogenated hydrocarbons such as polychlorinated biphenyls ("PCBs") and similar toxic materials. In general, superoxide ions are useful reducing agents.

U.S. Pat. No. 3,998,936 to Ernst et al. discloses a process for regenerating the activity of the catalyst used in the hydrogenation (or reduction) stage of the cyclic anthraquinone process for producing hydrogen peroxide involving the use of a platinum group metal catalyst. However, Ernst et al. does not disclose how an overall oxidation/reduction system could be constructed that would have broad application.

U.S. Pat. No. 4,751,068 to Bicker et al. discloses a method of catalyzing oxidation/reduction reactions of simple molecules through the redox catalytic activity of chelating agents complexed with a metal atom (the complex being referred to as a "chelate"). These chelates have been shown to be useful in converting CO and $H_2O$ to $CO_2$, CO and $H_2S$ to COS, CS and $H_2S$ to $CS_2$, CO and $NH_3$ to CONH, and CO and $RNH_2$ to RNCO. However, in order to regenerate the spent chelates it is necessary to react the chelates with oxidants or reductants. No self-sustaining reaction sequence is disclosed in Bicker et al.

More recently, with the advent of more refined biochemical techniques, biologically induced oxidations and reductions have been carried out using, e.g., fungi and agents which are secreted thereby. These biologically derived reactions are often superior to simply adding oxidation and/or reducing agents to a reaction mixture because of their lower cost and greater ability to more carefully control the reaction conditions, especially those reactions which involve the use of enzymes. Enzymes have the advantage being able to overcome high reaction barriers without the input and/or generation of large amount amounts of energy such as heat. In addition, as long as the biological agent is kept alive by ensuring that the system has adequate quantities of nutrients (some or all of which are supplied by the chemicals targeted for degradation) it will continue to produce adequate quantities of the oxidation or reduction agents. In this manner, the reaction is often self-sustaining so that no new reactants need to be added to complete the oxidation and/or reduction reactions.

There are numerous examples of biologically induced degradation of organic molecules. For example, lignin, which is the structural polymer found in wood and a substance which is otherwise highly resistant to many forms of biodegradation, is readily degraded in the presence of the white rot fungus *Phanerochaete chrysosporium*. Kirk, T. et al., *Arch. Microbiol.* 117:277–85 (1978). Lignin degradation is catalyzed by a group of enzymes including extracellular peroxidases secreted by *P. chrysosporium* under nutrient nitrogen-limiting conditions. Gold, M. et al., *Arch. Biochem. Biophys.*, 234:353–62 (1984); Tien, Met al., *Proc. Natl. Acad. Sci. USA,* 81:2280–84 (1984). It is known that both lignin peroxidases ("LiP") and manganese-dependent peroxidases are produced by white rot fungi. Glenn, J. et al, *Arch. Biochem. Biophys.*, 242:329–41 (1985). The fungi also produce enzymes that generate hydrogen peroxide. Kelley, R. et al, *Arch. Microbiol.,* 144:248–53 (1986); Kersten, P., *Biochemistry,* 87:2936–40 (1990). Veratryl alcohol (3,4-dimethoxybenzyl alcohol) is a secondary metabolite of *P. chrysosporium* and is also believed to be involved in lignin degradation. Harvey, P. et al., *FEBS Lett.,* 195:242–46 (1985).

In addition, the degradation of several environmental pollutants to carbon dioxide by white rot fungi has also been reported. U.S. Pat. No. 4,891,320 to Aust et al; Bumpus, J. et al., *Science,* 228:1434–36; Ryan, T. et al., *Appl. Microbiol. Biotechnol.,* 31:302:07 (1989); Fernando, T. et al, *Appl. Microbiol. Biotechnol.,* 56:1666–71 (1990); Kennedy, D. et al., *Appl. Microbiol. Biotechnol.,* 56:2346–53 (1990).

Although these articles generally discuss the use of white rot fungi to degrade lignin, no specific information as to the mechanism of this degradation is revealed. To the extent that certain intermediate substances such as LiP or veratryl alcohol have been shown to be involved, these articles do not contain information that would teach how to utilize white rot fungi or other useful organisms in a variety of oxidation or reduction reactions to generally oxidize or reduce any organic compound.

In the last few decades, there has been growing concern about the accumulation of toxic organic pollutants in the soil and water. Many industrial operations, particularly those involving chemical processes, have resulted in the contamination of huge amounts of soil, which in turn pollutes ground water and streams. With the fairly recent passage of stricter environmental legislation mandating the cleanup of what are referred to as "remediation sites" there has arisen a great need for practical and economically viable methods of soil and water remediation.

In the case of toxic organic pollutants such as chlorinated hydrocarbons, PCBs, and other organic solvents, the primary method of removing these from the soil involves the temporary removal of the contaminated soil, which is then passed through large columns through which hot air is passed. This causes the volatile contaminants to be driven off by evaporation. However, not only is this method extremely expensive, it does not guarantee the removal of the pollutants from the environment but simply shifts them from the ground into the air. While some degradation of these pollutants may occur in the presence of sunlight, many of the less reactive compounds are simply scattered into the air where they might later precipitate back into the earth, albeit in a more diluted form.

While organisms such as white rot fungi have been shown to degrade certain toxic pollutants in the laboratory, their use as general agents to clean up such toxic pollutants has been limited due to the lack of understanding of the reaction mechanisms involved in their oxidation and reduction. In addition, because many of the most persistent pollutants exist deep beneath the earth it has not been possible to sustain living white rot fungi or other organism cultures in the highly anaerobic conditions which exist beneath the earth. Finally, without an understanding of the necessary intermediates, or "diet" of the reactions involving the degradation of certain organic materials through the use of such organisms it has heretofore been impossible to control, or even predict, the types of organic substances that might be degraded through such mechanisms.

From the foregoing it should be understood that what are needed are compositions and methods which can be generally employed to carry out any number of oxidations or reductions on any targeted organic substrate. Moreover, it will be appreciated that it would be a significant advancement of the art if such compositions and methods could be cheaply and easily carried out by using relatively inexpensive raw materials, such as those used to grow white rot fungi.

It would yet be a significant improvement over the prior art if such compositions and methods could be varied to alternatively reduce, oxidize, or both, depending on the substrates to be degraded. Specifically, it would be a major advancement in the art if both the oxidative and reductive properties could be carefully controlled so that compounds requiring both oxidation and reduction for their degradation can be fully degraded utilizing a single reactive system, or different systems or conditions in series.

It would yet be a significant improvement over the prior art to provide compositions and methods under a variety of conditions which could degrade a variety of recalcitrant environmental pollutants such as PCBs, chlorinated hydrocarbons, and other toxic organic wastes without having to physically alter the reaction conditions once the reactions are set in motion. In addition, because living organisms are typically employed to carry out these reactions, it would be a major advancement in the art if such compositions and methods resulted in the generation of sufficient molecular oxygen so that the organisms would stay alive even under extremely anaerobic conditions, such as in remediation sites where the organisms are injected deep into the contaminated soil.

Such compositions and methods are disclosed and claimed herein.

BRIEF SUMMARY AND OBJECTS OF THE INVENTION

The present invention involves the use of free radical generating catalysts to initiate a variety of different, yet related, oxidation and/or reduction reactions. Free radicals can be formed by chemical, biological, photochemical or electrochemical methods. A preferred method of forming the free radicals involves the use of living organism, such as white rot fungi, which are known to secrete LiP, a free radical generating catalyst. The LiP is usually activated by an electron acceptor such as $H_2O_2$ and then reacts with an oxidant precursor (or "mediator) to form the free radical of the mediator. The free radical of the mediator is a strong oxidizing agent which can be used to generally carry out a number of desired oxidation reactions.

For example, the free radical of the mediator can be used to directly oxidize, and thereby degrade, a targeted substrate. In addition, the free radical of the mediator can be used to generate molecular oxygen, which is often desired in order to sustain the life of an organism if organism driven reactions are involved. Finally, the free radical of the mediator can be used to form the free radical of certain reductants, which are strong reducing agents. Thus, depending upon the constituents in the reaction site, any or all of these various reactions can be simultaneously carried out. Moreover, because most of the necessary reaction constituents are secreted by white rot fungi, such reactions can be substantially self-sustaining, although it may be important to initially adjust the concentrations of the required substances for any given reaction system.

Preferred free radical generating catalysts include LiP and MnP secreted by white rot fungi, horse radish peroxidase, and lactoperoxidase. Preferred mediators include veratryl alcohol, also secreted by white rot fungi and Mn II. In addition, methoxybenzenes (such as 1,2,3-trimethoxybenzene, 1,4-dimethoxybenzene, 1,2,4-trimethoxybenzene), iodide, and ABTS can be used in place of veratryl alcohol.

The reaction of the free radical generating catalyst and the stated mediators yields the veratryl alcohol cation radical, Mn III, the ABTS cation radical, or the cation radical of the methoxybenzene involved. In most cases, the free radical of the mediator can be used to carry out a variety of oxidation reactions. However, in the case of the iodide radical, iodination of organic molecules can occur unless a suitable reductant, as more fully discussed below, is added to arrest the iodination process.

Preferred reductants include organic acids such as oxalic acid, EDTA, hydroquinones, and the superoxide molecule, which is converted to molecular oxygen by this scheme. In the case of organic acids or hydroquinones, these reductants are converted into their free radical analogs, which can be used to reduce any number of electron acceptors.

In one embodiment of the present invention, the free radical of the reductants are used to reduce chlorinated hydrocarbons such as $CCl_4$, which results in its dechlorination. However, the present reaction could be used to generally dehalogenate any number of halogenated organic substances, such as PCBs, DDT, TCDD, etc.. Other organic substances which can be reduced include NBT and cytochrome c.

In addition, the free radical of the reductants can react with molecular oxygen to form the superoxide anion radical. If ferric iron is present, it is reduced to ferrous iron which can generate hydroxyl radical, a well known, powerful oxidant, via the Haber-Weiss reaction.

Therefore, through a series of simultaneous or sequentially induced reduction and oxidation reactions, molecules such as PCBs can first be dehalogenated in a reduction reaction, and then oxidized to $CO_2$ in an oxidation reaction. Because the free radical of the mediator is reduced by the reductant, the mediator is generally continuously regenerated during a reaction involving such reductants. However, because the anion radical of the organic acid is further oxidized during the dechlorination reaction, which often results in the decarboxylation of the organic acid and the generation of $CO_2$ gas, the organic acid is thus depleted during this reaction scheme. However, because one of the metabolic byproducts of white rot fungi is oxalic acid, it is often possible to sustain the reaction scheme without having to continuously add additional oxalate ions.

Following the general scheme set forth above it is possible to specifically produce particular radicals having particular redox potentials useful for catalyzing a wide variety of different oxidation or reduction reactions. In particular, the compositions and methods of the present invention allow for the production of superoxide, hydroxyl, iodide, organic acid, and semiquinone radicals. Each of these radicals have different redox potentials suitable for catalyzing any number of oxidative, reductive, or both types of reactions. As a result, the compositions and methods of the present invention are capable of degrading a wide variety of chemicals (from highly oxidized to highly reduced).

Specifically, anion radicals of, for example oxalate or EDTA, have been shown to be useful in the degradation of $CCl_4$. Superoxide is known to reduce molecules like DDT, while hydroxyl radicals are known to be the most powerful oxidants. PCBs and many other recalcitrant chemicals are known to be oxidized by hydroxyl radicals.

The methods of the present invention are far more economical than previously known methods for carrying out similar oxidation and/or reduction reactions as they can be carried out at room temperature and atmospheric pressure. Furthermore, the raw materials necessary to carry out the reactions of the present invention are very inexpensive in comparison to previously known methods of oxidizing, for example, toxic pollutants such as $CCl_4$, PCBs, DDT, and other recalcitrant organic materials.

More importantly, because the mechanisms of the various reactions involved in the present invention are understood they can more easily be controlled. This includes both the rate as well as the particular reaction that is involved, including being able to choose the targeted substrate to be oxidized, reduced, or otherwise degraded. Thus, by simply altering the identities and concentrations of the raw materials added to a reaction site, as well as the pH, the process can be tailored to degrade a wide variety of organic substances, including halogenated hydrocarbons.

Moreover, none of the raw materials used in the methods of the present invention are hazardous but are environmentally friendly.

From the foregoing it should be understood that an object of the compositions and methods of the present invention is the ability to carry out any number of specifically tailored oxidation and/or reduction reactions. Another object of the present invention is the ability to carry out such oxidation and/or reduction reactions far more cheaply and easily because they require relatively inexpensive and easily obtainable raw materials, such as white rot fungi.

Yet another object of the present invention is the ability to carry out such oxidation/reduction reactions using fungi and conditions which affect the production of mediators (such as veratryl alcohol) and reductants (such as oxalate).

More specifically, an object of the present invention is the ability to design a reaction sequence by altering the identities and amounts of the constituent materials to alternatively reduce and/or oxidize certain targeted substrates depending on the desired result. Moreover, such oxidation and reduction reactions can be carried out without having to greatly alter the reaction conditions, such as continuously adding more oxidant or reductant because such agents are continuously regenerated.

Yet another object of the compounds and methods of the present invention is the targeted degradation of a variety of recalcitrant environmental pollutants such as PCBs, chlorinated hydrocarbons, and other toxic organic wastes.

Still, a further object of the compositions and methods of the present invention is the ability to generate oxygen necessary to sustain the life of organisms which must often be employed in highly anaerobic conditions, such as in the case of remediation sites where the organisms are injected deep into contaminated soil.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

BRIEF DESCRIPTION OF THE DRAWINGS

FIG. 8, the effect of $H_2O_2$ concentrations between 0.125 and 40 mM; FIG. 9, the effect of $H_2O_2$ concentrations between 0.125 and 1.5 mM on veratryl aldehyde formation (♦) and $O_2$ production (■). The values in FIG. 9 represent the mean of triplicate measurements with error bars indicating the standard deviations.

DETAILED DESCRIPTION OF THE PREFERRED EMBODIMENTS

This invention relates to compounds and methods for carrying out oxidation reactions, reduction reactions, and mixtures of both depending on the reaction conditions and constituent chemicals that are added to the reaction mixture. More specifically, the invention relates to compounds and methods wherein a free radical generating catalyst is used to react with a mediator to form the free radical of the mediator. Often this free radical is a cation radical which, being electron deficient, is a strong oxidizing agent. It can be used directly to oxidize, and thereby degrade, a targeted organic substrate, or it can be reacted with a suitable organic chemical (or "reductant") to form the free radical of the reductant, commonly an anion radical, which is a strong reducing agent. Using either the cation radical oxidant, the anion radical reductant, or both, a wide variety of oxidation or reduction reactions or both may be carried out, such as for the degradation of recalcitrant toxic organic chemicals found, for example, in toxic waste sites.

Under the Superfund laws passed in 1980 ("CERCLA") many remediation sites in the United States must be cleaned up. The pollutants in these sites include a variety of toxic chemicals, including PCB's, chlorinated hydrocarbons, and other pernicious substances not generally subject to normal biodegradation reactions. These substances and others have proven extremely difficult to remove or destroy.

One method is simply to dig up large amounts of earth and put them into tall columns which are heated by air, thereby driving off the chemicals. One obvious shortfall of this method is that the chemicals are merely transferred from the soil into the air. Under the present invention, substances such as chlorinated hydrocarbons are first reduced to strip off the chlorine moieties, and then oxidized to $CO_2$.

In addition, the present invention provides methods for producing molecular oxygen, which is often necessary to sustain the viability of living organisms such as white rot fungi.

I. General Reaction Scheme.

Figure 1:
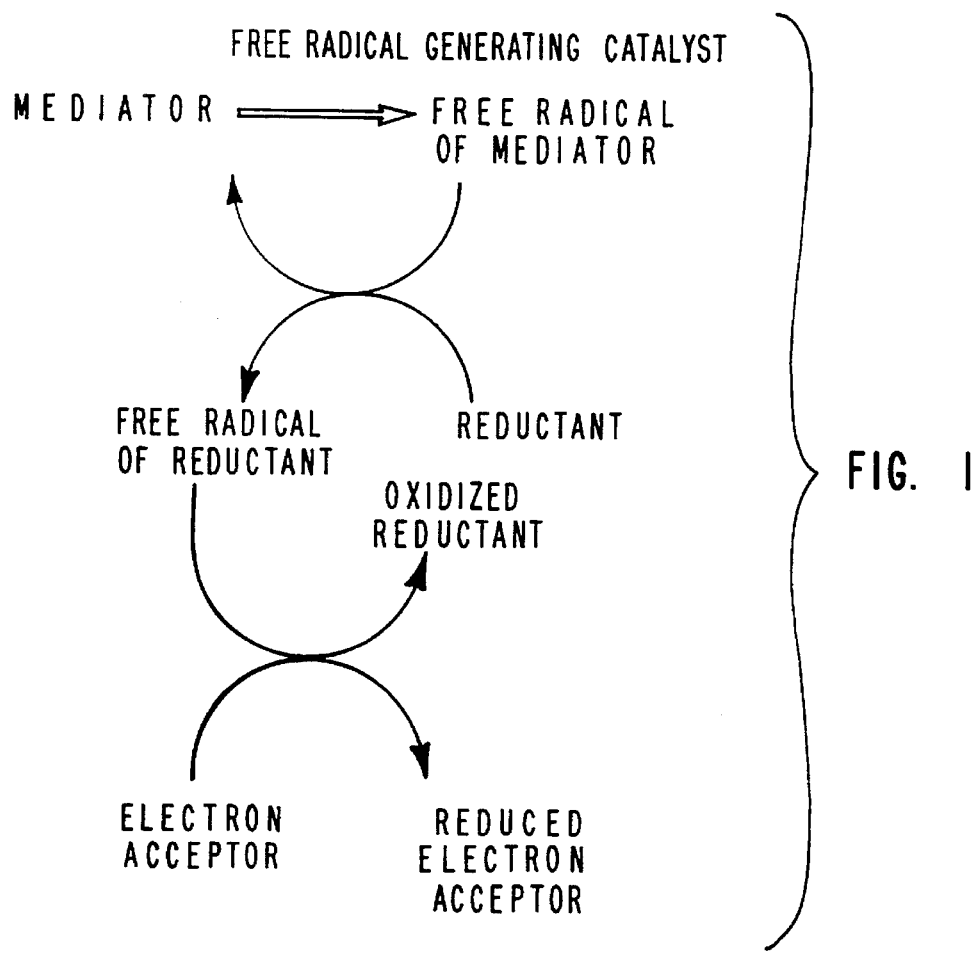
FIG. 1 is a representation of the total general reaction scheme of the present invention (with the understanding that not all of the reactions shown therein must necessarily be employed in all situations).

Referring to FIG. 1, the general reaction scheme of the present invention is as follows: (1) a peroxidase is used to (2) react with a mediator (oxidant precursor) (3) to form the free radical of the mediator, which is a strong oxidant; (4) the free radical of the mediator then reacts with and oxidizes a reductant (5) to form the radical of the reductant (regenerating the mediator); (6) the free radical of the reductant is a strong reducing agent capable of reacting with an electron acceptor (7) which is reduced in the final step of the reaction sequence.

In any given reaction mixture, there may be multiple oxidations and reductions occurring simultaneously depending on the constituent materials, their concentrations, and the pH of the system. It should be understood that the reductant described in step 4 has heretofore been viewed as merely an inhibitor of the oxidative nature of the free radical of the mediator. Not until this invention has it been understood that the reductant can actually be converted into a powerful reducing agent. Shah., M. et al., *On the Mechanism of Inhibition of the Veratryl Alcohol Oxidase Activity of Lignin Peroxidase H2 by EDTA, J. Biol. Chem.*, 267:21564–69 (October 1992). For purposes of disclosure this article is incorporated herein by specific reference. It is this understanding of the nature of the reductant that allows one to design a reaction sequence which can specifically target selected organic substances for degradation.

For example, in the case of chlorinated hydrocarbons, the molecules must first be reduced to remove the chlorine moieties (which are reduced to chloride ions). In the experiments set forth below, $CCl_4$ was chosen because of its extreme stability and resistance to degradation. Once it was learned that a reaction sequence could specifically be designed which would reduce $CCl_4$ to trichloromethyl radical (which is then degraded to $CO_2$).

Once the chlorine moieties have been removed from the chlorinated hydrocarbon, the remaining carbon containing molecules are easily oxidized to $CO_2$ by means of the free radical of the mediator.

This method of dehalogenation is contrary to the current understanding that LiP alone actually catalyzes the halogenation of organic molecules. Nevertheless, halogenation reactions are inhibited and actually reverse to create dehalogenation conditions according to the present invention. Shah, M. et al, *Oxidation of Halides by Peroxidases and Their Subsequent Reactions, Arch. Biochem. Biophys.*, 300:000 (January 1993). For purposes of disclosure this article is incorporated herein by specific reference.

In addition to the free radical of the mediator, hydroxyl radicals, the most powerful oxidant known, can be produced according to the present reaction. A more thorough discussion of how to generate hydroxyl radicals is set forth in Barr, D. et al, *Production of Hydroxy Radical by Lignin Peroxirane, Arch. Biochem. Biophys.*, 298:480–85 (November 1992). For purposes of disclosure, this article is incorporated herein by specific reference. This article demonstrates that the hydroxyl radical is obtained after the final step of the general reaction sequence wherein molecular oxygen is reduced to superoxide anion radical during the decarboxylation of the anion radical of either EDTA or oxalate. Superoxide is known to catalyze the production of hydroxyl radical in the presence of ferric ion via an iron dependent Haber-Weiss reaction. This article confirms that this reaction also occurs under the reaction conditions of the present invention.

Finally, the presence of molecular oxygen where none was initially present led to another study to be published in a paper by Barr, D. et al, entitled *Veratryl Alcohol-dependent Production of Molecular Oxygen by Lignin Peroxidase, J. Biol. Chem.*, 268:14 (Jan. 1993). The studies set forth in this unpublished article demonstrate that both superoxide and molecular oxygen can be produced where hydrogen peroxide is the reductant which reacts with veratryl alcohol. By this mechanism hydrogen peroxide is oxidized to superoxide molecule, which then dismutates into molecular oxygen and hydrogen peroxide. However, whether molecular oxygen is consumed or produced is dependent upon the concentration of hydrogen peroxide (and other reductants such as oxalate), which is also necessary in many cases to activate the peroxidase to begin the reaction sequence. More specific details regarding these findings are set forth below.

II. Preferred Constituents and Their Reactions.

Preferred peroxidases include LiP, horse radish peroxidase, and lactoperoxidase. Each of these peroxidases are activated by hydrogen peroxide to form an activated 2-electron oxidized enzyme intermediate. It is this enzyme intermediate, being electron deficient, which reacts with the mediator to form the free radical of the mediator. In fact, because the enzyme intermediate is deficient of two electrons, one mole of the enzyme intermediate is normally able to react with two moles of mediator to form two moles of the free radical of the mediator.

Preferred mediators include veratryl alcohol, ABTS, Mn II, iodide, 1,2,3-trimethoxybenzene, 1,4-dimethoxybenzene, and 1,2,4-trimethoxybenzene. Each of these mediators is oxidized by the enzyme intermediate to form a free radical of the mediator. In the case of veratryl alcohol, methoxybenzenes, or ABTS, the cation radical is formed. The use of iodide or Mn II provides a method for the formation of neutral radicals, while the use of any of the others provides a method for the formation of cation radicals of different redox potentials. In addition, in the case of ABTS the cation free radical can be formed by non-enzymatic, electrochemical means. However, the use of enzymes allows for more carefully controlled and economical production of radicals (either oxidative or reductive).

Preferred reductants include EDTA, oxalate, hydroquinones, hydrogen peroxide, and quinones plus quinone reductases. Of the reductants, only oxalate, quinone with quinone reductase, and hydrogen peroxide are secreted by white rot fungi. Depending on the desired reactions, this fact must be taken into consideration, either to take advantage or inhibit the reactions which involve either oxalate or hydrogen peroxide. (The same is true for veratryl alcohol, which is also secreted by white rot fungi.)

One mole of reductant is oxidized by one mole of the free radical of the mediator to form one mole of the free radical of the reductant. In each case the anion radical of the reductant is formed. The anion radicals of either EDTA or oxalate are further oxidized during the next reactive step with the electron acceptor and decarboxylated. The anion radical of hydrogen peroxide (or superoxide) is further oxidized to molecular oxygen. Finally, the anion radical of the hydroquinones (semiquinones) are further oxidized to their quinone analogs during the final reactive step of the reaction sequence of the present invention.

In the case of the use of manganese dependent peroxidases, wherein Mn II is the mediator and is oxidized to Mn III, preferred reductants will be either hydroquinones or quinones plus quinone reductase to catalyze the reductive reactions.

Suitable electron acceptors, which are reduced by the anion radicals of the reductant, can be any organic molecule which is targeted for degradation but is usually a halogenated hydrocarbon such as $CCl_4$, DDT, TCDD (2,3,7,8-tetrachlorodibenzo-p-dioxin) (commonly known as "dioxin"), lindane (1,2,3,4,5,6,-hexachlorocyclohexane), and PCBs. In addition, molecular oxygen can act as the electron acceptor and be converted to superoxide, a powerful reductant, which in turn can reduce chlorinated hydrocarbon or further react with ferric ion via Haber-Weiss reactions to form the hydroxyl radical, a powerful oxidant. Other electron acceptors which have been proven to work include NBT and cytochrome c.

In the case where hydrogen peroxide was the reductant, and superoxide dismutates (or reacts with itself) to form hydrogen peroxide and molecular oxygen, one equivalent of superoxide is acting as the reducing agent, while a second equivalent of superoxide is acting as the electron acceptor. The first equivalent of superoxide is oxidized to molecular oxygen, while the second equivalent of superoxide is reduced to hydrogen peroxide. In this manner, the inclusion of hydrogen peroxide as the reductant still follows the generalized reaction scheme of the present invention.

From the foregoing, it should be understood that the reactions of the present invention allow for the formation of superoxide, hydroxyl, iodide, organic acid, semiquinone radicals, and combinations of any of them, of very different redox potentials. Hence, the present invention is suitable for catalyzing both oxidative and reductive reactions on a variety of organic substrates.

III. Reactions Involving White Rot Fungi.

White rot fungi, such as *Phanerochaete chrysosporium*, are known for their ability to degrade lignin to carbon dioxide. Some of the important components of the lignin degrading enzyme system of the fungi are lignin peroxidase, veratryl alcohol and $H_2O_2$. In addition to lignin, the fungi are known to mineralize a variety of recalcitrant chemicals such as $CCl_4$, DDT, TCDD, Lindane, and PCBs to carbon dioxide. Although white rot fungi were previously shown to be able to degrade halogenated chemicals, the mechanism was heretofore never understood. Hence, controlled, sustainable reactions could not be carried out on a large scale, such as under conditions relating to the remediation of toxic waste sites. In particular, dehalogenation by LiP alone has never been demonstrated. In fact, LiP has been reported to be a haloperoxidase. Ranganathan, V. et al., *Biochemistry*, 26:5127–32 (1987); Farhangrazi Z. et al., *Biochemistry*, 31:10763–68 (1992).

Therefore, the focus of most researchers has been towards the oxidative reactions of LiP instead of the reductive reactions of LiP of the present invention. Because chlorinated organic materials are highly electron deficient they cannot be oxidized by the enzyme or the free radical of the mediator. For the reductive dehalogenation of these chemicals, reducing reaction conditions are required. According to the present invention it has been discovered that LiP is able to catalyze reduction reactions using organic acids like EDTA or oxalate as a reductant and veratryl alcohol as a free radical mediator. Shah, M. et al., *On the Mechanism of Inhibition of the Veratryl Alcohol Oxidase Activity of Lignin Peroxidase H2 by EDTA, J. Biol. Chem.*, 267:21564–69 (October 1992); Barr, D. et al., *Production of Hydroxyl Radical by Lignin Peroxidase From Phanerochaete chrysosporium, Arch. Biochem. Biophys.*, 298:480–85 (November 1992).

These studies demonstrated the oxidation of organic acids to anion radicals by veratryl alcohol cation radical, produced by LiP. The organic acid radicals were shown to reduce various electron acceptors such as cytochrome c, NBT, ferric iron and molecular oxygen. This finding led to the investigation into the possible reduction of halogenated organic materials by a similar mechanism. In this study $CCl_4$ was used as a representative halogenated organic material as it is a well known electron acceptor.

The data presented herein indicate that $CCl_4$ is first reduced to trichloromethyl radical by the reductive reactions of lignin peroxidase in a reaction mixture containing lignin peroxidase H2, veratryl alcohol, $H_2O_2$, and EDTA. These results suggest that the reduction of $CCl_4$ to trichloromethyl radical is a free radical mediated, three-step process, where veratryl alcohol is the free radical mediator, EDTA the reductant, and $CCl_4$ an electron acceptor.

The first step is the oxidation of veratryl alcohol to the veratryl alcohol cation radical by LiPH2; the second step is the oxidation of EDTA to the anion radical of EDTA by the veratryl alcohol cation radical; and the third step is the reduction of $CCl_4$ to the trichloromethyl radical by the EDTA anion radical, with the concomitant oxidation and decarboxylation of EDTA. The trichloromethyl radical, which is far more unstable than $CCl_4$, is subsequently dehalogenated under the reductive conditions which are present. Thus, it is now understood for the first time that the reduction of halogenated organic materials can be carried out using LiP as long as a sufficient amount of reductant is present to react with the free radical of the mediator. Based on this novel finding, as well as other knowledge gathered by the studies relating to the production of molecular oxygen, the generalized scheme set forth above is proposed for the degradation of halogenated organic chemicals by *P. chrysosporium*.

EXPERIMENTAL PROCEDURES

Materials: Hydrogen peroxide, PBN and Tempol were obtained from Sigma Chemical Company (St. Louis, Mo.). Veratryl alcohol and DMPO were purchased from Aldrich Chemical Company (Milwaukee, Wis.). EDTA was purchased from Mallinckrodt (Paris, Ky.). Buffers and reagents were prepared with purified water (Barnstead Nanopure 11 system specific resistance 18.0 megohm - cm). Carbon tetrachloride was purchased from EM Science (Gibbstown, N.J.). Carbon-13 labeled $CCl_4$ was purchased from MSD Isotopes (Montreal, Canada).

Lignin Peroxidase H2 Production and Purification: Culture conditions for the production of lignin peroxidase H2 from *P. chrysosporium* and its purification were as previously described in Tuisel, H. et al, *Arch. Biochem. Biophys,* 279:158–66 (1990). For purposes of disclosure, this article is incorporated by specific reference. Lignin peroxidase H2 (75 U/mg) was used for all the experiments.

Spin Trapping of Trichloromethyl, EDTA and Superoxide Radicals: The trichloromethyl radical was detected by electron spin resonance (ESR) spectroscopy as its spin adduct with PBN. Reaction mixture contained 0.1M chelex treated sodium phosphate buffer, pH 6.0, 25 µM lignin peroxidase H2, 4 mM EDTA, 500 µM $H_2O_2$, 1% $CCl_4$, 90 mM PBN, and 1 mM veratryl alcohol. Spectral recording began within 1 minute following the initiation of reaction with 500 µM $H_2O_2$. ESR spectra were recorded at room temperature using a Varian E-109 spectrometer operating at 9.5 GHz with 100 KHz modulation frequency. Hyperfine splitting constants were determined by comparison with the standard Tempol using 17.1 G for $a_N$ in water.

The EDTA derived radicals were detected under similar conditions in reaction mixtures without $CCl_4$. Superoxide radicals were detected in these reaction mixtures without $CCl_4$ by increasing the pH to 6.5 and using 60 mM DMPO as the spin trap.

Anaerobic reactions were performed by purging each component of the reaction mixture, the reaction mixture itself, and the ESR cavity with nitrogen gas for 10 minutes.

Figure 2:
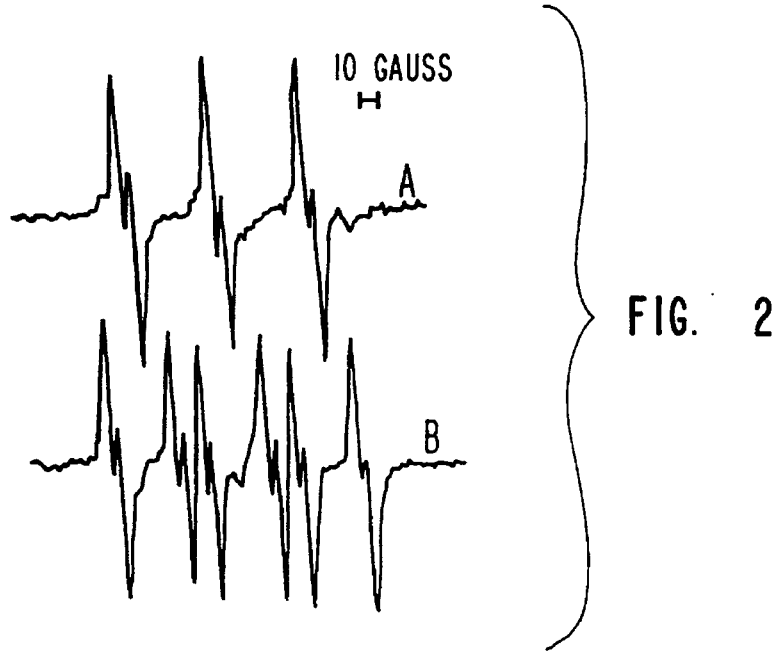
FIG. 2. ESR spectra of PBN-$CCl_3$ radical adducts. (A) The reaction mixture contained lignin peroxidase H2. $H_2O_2$ veratryl alcohol, EDTA, $CCl_4$ and PBN (see Material and Methods for concentrations). (B) The conditions were the same as described in (A) except that $^{13}CCl_4$ was substituted for $CCl_4$. The spectrometer settings were: scan range 100 G, modulation amplitude 10 G, gain $1\times10^4$, microwave power 50 mW,, time constant 0.128 sec, scan time 2 minutes.

As indicated by FIG. 2A, LiPH2 reduced $CCl_4$ to the trichloromethyl radical in a reaction mixture containing $H_2O_2$, veratryl alcohol, EDTA, and PBN. The ESR splitting constants of the spin adduct were $a_N=14.0$ G, $a_H^\beta=1.8$ G. These values are in agreement with those reported previously for the PBN-trichloromethyl radical spin adduct. Janzen, E. et al., *Environ.. Hlth, Persp.*, 64:151–70 (1985) ("Janzen et al"). To further confirm the identity of the trichloromethyl radical, $^{13}CCl_4$ was used. The ESR spectrum of PBN spin adduct is shown w in FIG. 2B. The ESR splitting constants were found to be $a_N=14.0$ G, $a_B^H=15$ G, and $a_\beta^{13}C=9.6$ G. These values are also in agreement with those reported previously for the PBN-$^{13}$C-labeled trichloromethyl radical spin adduct. Janzen et al.

Figure 3:
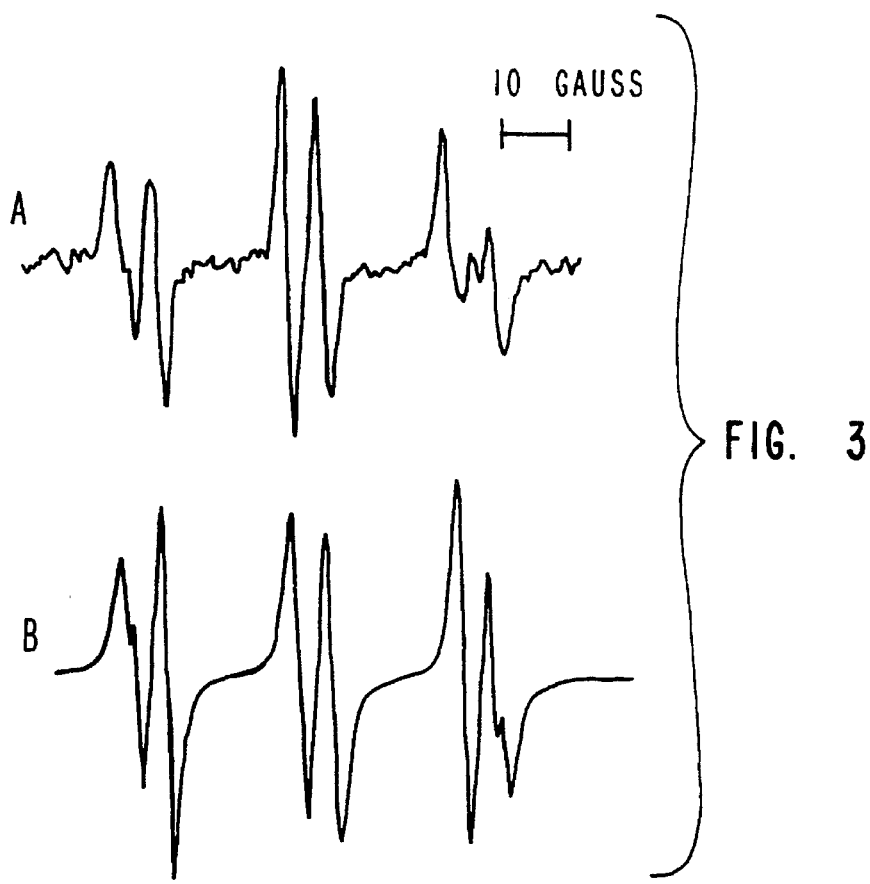
FIG. 3. ESR spectra of PBN adducts with EDTA derived radicals. (A) Reaction conditions were similar to those described in FIG. 1 except $CCl_4$ was omitted. The spectrometer settings were: scan, range 100 G, modulation amplitude 1.0 G gain $2.5\times10^4$, microwave power 50 mW, time constant 0.5 sec, scan time 4 minutes. (B) Computer simulated spectra of the two major PBN adducts in A. The hyperfine splitting constants used were (i) $a_N$=15.6 G, $a_H\beta$= 3.04 G, (ii) $a_N$=16.3 G, $a_H\beta$=4.07 G.
Figure 4:
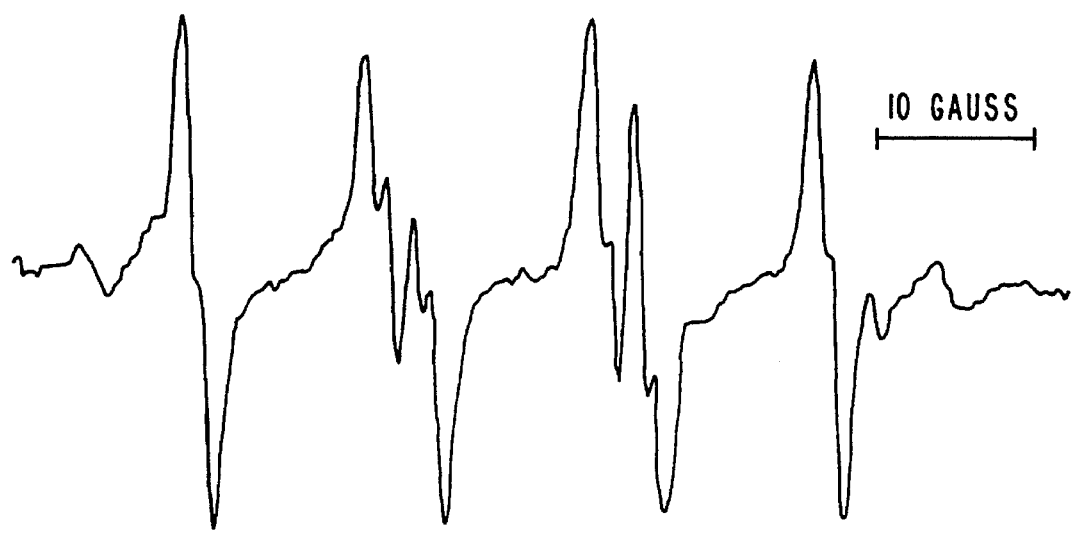
FIG. 4. ESR spectrum of DMPO-superoxide radical adduct. The reaction conditions were similar to those described in FIG. 1 except $CCl_4$ was omitted, the pH was 6.5, and DMPO was used as the spin trap. The spectrophotometer settings were: scan range 100 G; modulation amplitude 10 G; gain $8\times10^3$, microwave power 50 mW; time constant 0.128 sec; and scan time 2 minutes; modulation amplitude i 0 G; gain 8×10³, microwave power 50 mW; time constant 0.128 sec; and scan time 2 minutes.

Upon removal of $CCl_4$, the ESR spectrum was a mixture of carbon-centered radicals (FIG. 3A). Computer simulation of the two major spin adducts from these spectra is shown in FIG. 2B. The hyperfine splitting constants used in this simulation were $a_N=15.6$ G, $a_H^\beta=3.04$ G for one radical, and $a_N=16.3$ G, $a_H^\beta=4.07$ G for the other. These values were the same as that reported by us for EDTA radicals. Shah et al., *J. Biol. Chem.*, 267:21564–69 (1992). When DMPO was used as a spin trap, superoxide radicals were trapped in a reaction mixture containing lignin peroxidase H2, $H_2O_2$, EDTA and veratryl alcohol (FIG. 4). The hyperfine splitting constants were $a_N=14.3$ G, $a_H^\beta=11.7$ G, $a_H$ 1.3 G. These values are in agreement with values in the literature. Buettner, G., *Free Rad. Biol Med.*, 3:259–303 (1987). No DMPO-superoxide adduct was formed upon removal of enzyme, $H_2O_2$, veratryl alcohol or EDTA.

To check whether the EDTA radicals or superoxide was involved in the reduction of $CCl_4$, the reaction was studied under anaerobic conditions. PBN-trichloromethyl radical adducts were observed indicating EDTA radicals were able to reduce $CCl_4$.

Figure 5:
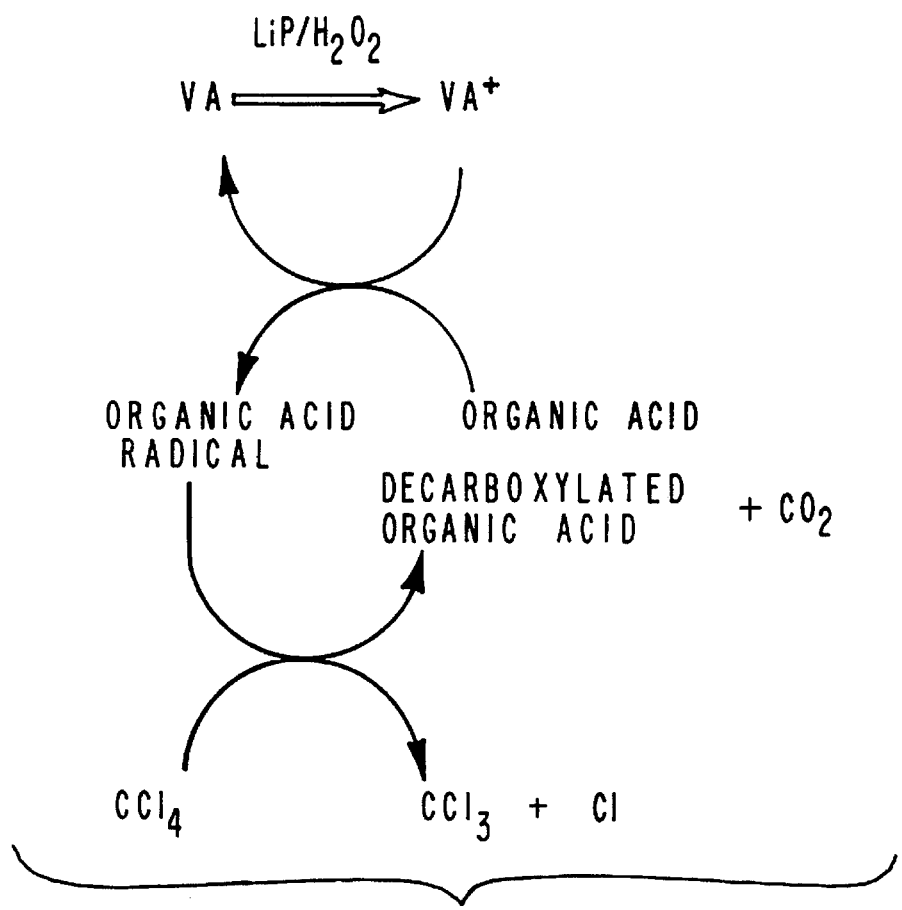
FIG. 5. The proposed scheme for the reduction of $CCl_4$ by lignin peroxidase H2. The organic acid is EDTA.

The proposed scheme for the reduction of $CCl_4$ by lignin peroxidase H2 in the reaction mixture containing EDTA, veratryl alcohol and $H_2O_2$ shown in FIG. 5 is as follows. First, veratryl alcohol is oxidized to the veratryl alcohol cation radical by lignin peroxidase H2 in the presence of $H_2O_2$. Then, the organic acid (i.e., EDTA) is oxidized to an organic acid radical by the cation radical of veratryl alcohol. The organic acid radical reduces $CCl_4$ to the trichloromethyl radical which results in the decarboxylation of the organic acid.

The proposed scheme is in agreement with previously reported mechanisms for the reductive reactions of lignin peroxidases. Shah, M. et al., *J. Biol. Chem.*, 267:21564–69 (1992); Barr, D. et al., *Arch. Biochem. Biophys.*, 298:480–85 (1992). It was shown that the cation radical of veratryl alcohol serves as the oxidant in the oxidation of EDTA to EDTA derived radicals, and the EDTA derived radicals in turn, serve as the reductant for the reduction of various electron acceptors, such as cytochrome c, NBT, molecular oxygen and ferric iron. In the present study, it was found that $CCl_4$ serves as an electron acceptor in this reductive system and was reduced under anaerobic, as well as aerobic conditions. EDTA radicals are proposed to be the reductant in the reduction of $CCl_4$ to the trichloromethyl radical.

The proposed scheme for the degradation of $CCl_4$ is also in agreement with the oxidative reactions of lignin peroxidase previously known in the art. Based on teachings known in the art it would seem safe to conclude that the oxidation of aminotriazole, $\alpha$-keto- -methiol-butyric acid, and malonic acid reductants by LiP should occur in the presence of the veratryl alcohol cation radical. That veratryl alcohol is transformed into the cation radical is confirmed by Gilardi, G. et al., *Biochem. Biophys Acta.*, 1041:129–32 (1990). For purposes of disclosure this article is incorporated herein by specific reference.

The proposed scheme has two major advantages with respect to the degradation of halogenated organic materials by white rot fungi. First, it provides an approach to inhibit the proven haloperoxidase reactions of LiP. It was also shown that the iodinating species (HOI or EOI, where E is enzyme) produced by peroxidases reacts with EDTA. In the process, EDTA was decarboxylated. Secondly, it suggests an approach for the degradation of highly halogenated organic materials. In this study we show that organic acid radicals could serve as the reductant for the reduction of $CCl_4$. In addition to superoxide and organic acid radicals, hydroxyl radicals can also be formed upon addition of ferric iron via the proposed oxidoreductive reactions of LiP. The degradation of halogenated organic materials by hydroxyl radicals is another alternative.

Among the components involved in the proposed scheme, EDTA is the only one which is not physiologically relevant. Future research is required to identify fungal reductants similar to EDTA. Oxalic acid and other organic acids are produced by white rot fungi. It should also be noted oxalic acid itself does not have the site for its halogenation. Haloalkanes are reported to react with amines upon photochemical activation. So, other potential physiologically relevant reductants would include amino acids which are functionally similar to EDTA. It is known that white rot fungi excrete proteases and the degradation of protein by proteases might be a possible source of such amino acids.

Another important finding was that the reduction of $CCl_4$ was performed in an aqueous media although organic radicals are considered to be hydrophobic. Hence, the reduction of $CCl_4$ would be expected to occur only in the organic phase, i,e., the $CCl_4$ phase. It is suggested that radicals are somehow being transferred from the aqueous phase to the $CCl_4$ phase. Since lignin is also hydrophobic like $CCl_4$, organic radicals produced by LiP probably attack lignin via a similar free radical mediated process.

It is also significant that like $CCl_4$, lignin is also a highly oxidized molecule. Therefore, the first step in the degradation of lignin might involve a reduction reaction by reducing radicals produced by LiP. Therefore, although not previously understood, it is highly probable that the degradation of lignin involves a combination of reductive and oxidative steps according the reactive scheme proposed by the present invention.

IV. Studies Relating to the Generation of Molecular Oxygen.

Although reported in the literature that veratryl alcohol prevents the deactivation of LiP in the presence of excess hydrogen peroxide, nothing was known regarding this mechanism. See Khadar, V. et al., *Biochem.*, 29:8535–39 (1990). In fact, studies leading up to the present invention showed that hydrogen peroxide can react with the cation radical of veratryl alcohol to form molecular oxygen via the formation of superoxide. This shows that hydrogen peroxide does not interfere with veratryl alcohol mediated LiP oxidations by reacting with LiP; rather excess hydrogen peroxide interferes with the oxidation reactions by reaction with the cation radical of veratryl alcohol, a powerful oxidant within the reactive scheme of the present invention. The result is the formation of superoxide anion radical, itself a powerful reductant rather than an oxidizer, while veratryl alcohol is reduced to its native state. Moreover, at least part of the hydrogen peroxide is regenerated upon the dismutation of superoxide to hydrogen peroxide and molecular oxygen. The proposed reaction scheme for the reaction of hydrogen peroxide and the cation radical of veratryl alcohol is as follows:

$$VA^+ + H_2O_2 \rightarrow VA + O_2^{-\cdot} + 2H^+ \quad \text{(Eq. 1)}$$

$$O_2^{-\cdot} + HO_2^{\cdot} + H^+ \rightarrow O_2 + H_2O_2 \quad \text{(Eq. 2)}$$

EXPERIMENTAL PROCEDURES

Chemicals—Hydrogen peroxide, oxalate, and superoxide dismutase were purchased from Sigma. Veratryl alcohol (3,4-dimethyoxybenzyl alcohol), anisole (methoxybenzene), 1,2,3-trimethoxybenzene, 1,4-dimethoxybenzene, and 1,2,4-trimethoxybenzene were purchased from Aldrich. 1,2,4,5-Tetramethoxybenzene was synthesized using the procedure of Kersten et al., *J. Biol. Chem*, 260:2609–12 (1985). The sodium acetate buffer was prepared using purified water (Barnstead NANO pure II system; specific resistance 18.0 Mohm-cm$^{-1}$).

Enzyme Production and Purification—The culture conditions used to produce lignin peroxidases and their purification and activity assay were as described previously in Tuisel, H. et al., *Arch. Biochem. Biophys.*, 279: 158–66 (1990) ("Tuisel et al."). The extracellular fluid was dialyzed overnight against 10 mM sodium acetate buffer, pH 6.0, and the proteins purified on a Mono Q HR 5/5 column (Pharmacia LKB Biotechnology Inc.). Veratryl alcohol oxidase activity in the extracellular fluid was determined by measuring an increase in absorbance at 310 nm (veratryl aldehyde formation) as described previously in Tuisel et al. The major lignin peroxidase (LiPH2) was used throughout this study.

Oxygen Consumption or Production Experiments—Oxygen consumption or production was measured using a Gilson oxygraph monitor equipped with a 1.8-ml water jacketed reaction chamber and a Clark type oxygen sensitive electrode. All reaction mixtures contained 0.63 μM LiPH2, 100 mM sodium acetate, pH 5.0, 3mM veratryl alcohol, and $H_2O_2$ and oxalate concentrations as indicated in the figure legends. The reactions were initiated by the addition of LiPH2. All reactions were performed at room temperature. In the experiment involving superoxide dismutase, 98 units/ml superoxide dismutase was added approximately 1 min after the reaction was initiated with LiPH2. The reactions involving superoxide dismutase were performed at pH 6.8 because its catalytic effect on the dismutation of $O_2$ is more marked at pH 6.8 than pH 5.0.

Spectral Characterization of LiPH2—The oxidation state of LiPH2 was determined by scanning between 600 and 480 nm. The concentrations of the reactants are described in the figure legends. All spectral recordings were made using a Shimadzu UV-160 spectrophotometer.

Figure 6:
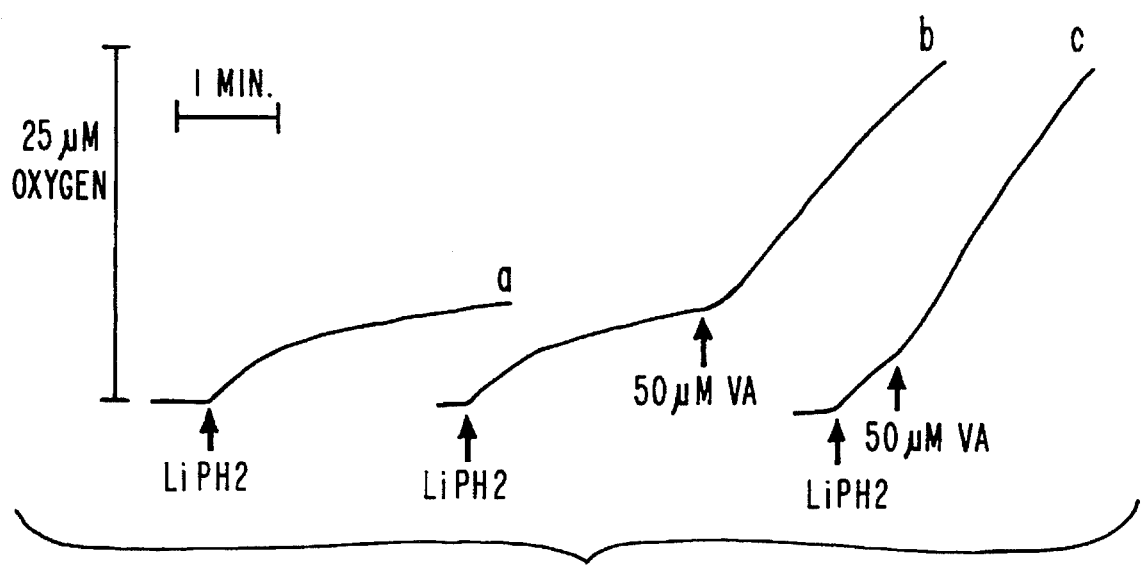
FIG. 6.
Figure 7:
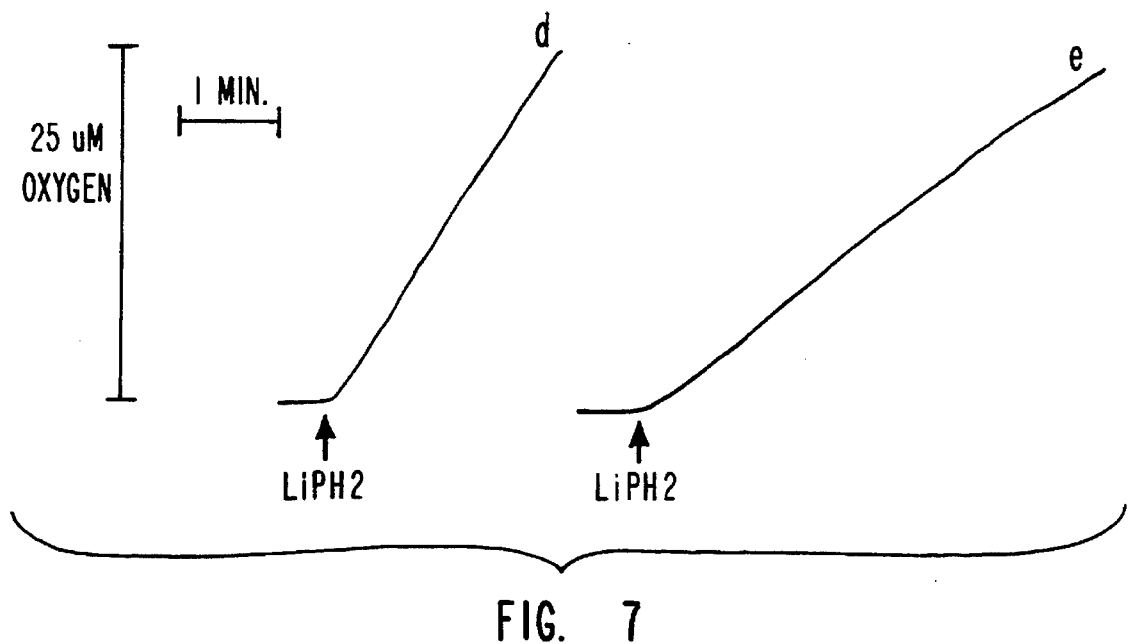
FIG. 7 Oxygen production in the presence and absence of veratryl alcohol. All reaction mixtures contained 100 mM sodium acetate, pH 5.0, 1 mM $H_2O_2$ and 0.63 µM LiPH2. The production of $O_2$ was measured in the absence of veratryl alcohol (a) with 50 µM veratryl alcohol (VA) added where indicated by the arrows (b and c), when 50 µM veratryl alcohol was added before initiating the reaction with LiPH2 (d) (of FIG. 7), and when 3 mM veratryl alcohol was added before initiating the reaction with LiPH2 (e) (of FIG. 7).

The effect of veratryl alcohol on LiPH2-catalyzed $O_2$ production is shown in FIGS. 6 and 7. Oxygen production was observed in the absence of veratryl alcohol (a). However, the addition of 50 µM veratryl alcohol at various times after initiating the reaction enhanced both the rate and extent of $O_2$ production (b, c, and d of FIG. 7) but to various degrees. When a saturating amount of veratryl alcohol (i.e., 3 mM) was added at the start of the reaction the $O_2$ production rate was 6 µM/min (e) (of FIG. 7).

Figure 8:
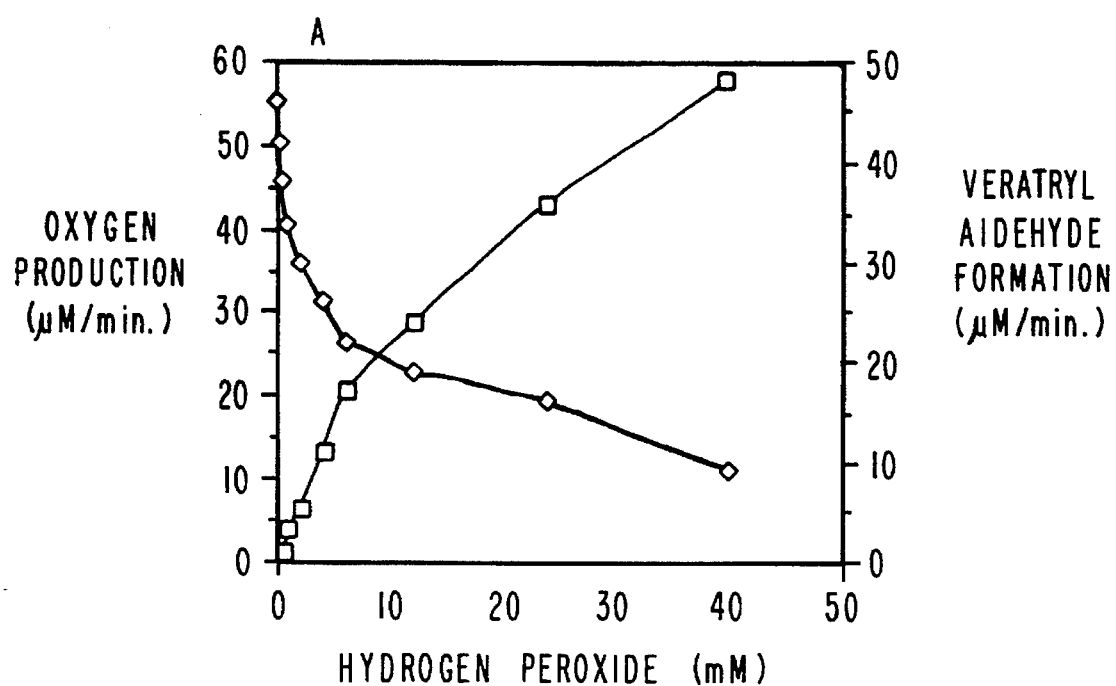
FIG. 8 and FIG. 9. Effect of hydrogen peroxide on the rates of LiPH2 catalyzed veratryl aldehyde formation and oxygen production. The reaction mixtures contained 100mM sodium acetate, pH 5.0, 0.63 µM LiPH2, 3 mM veratryl alcohol, and the indicated amounts of $H_2O_2$.
Figure 9:
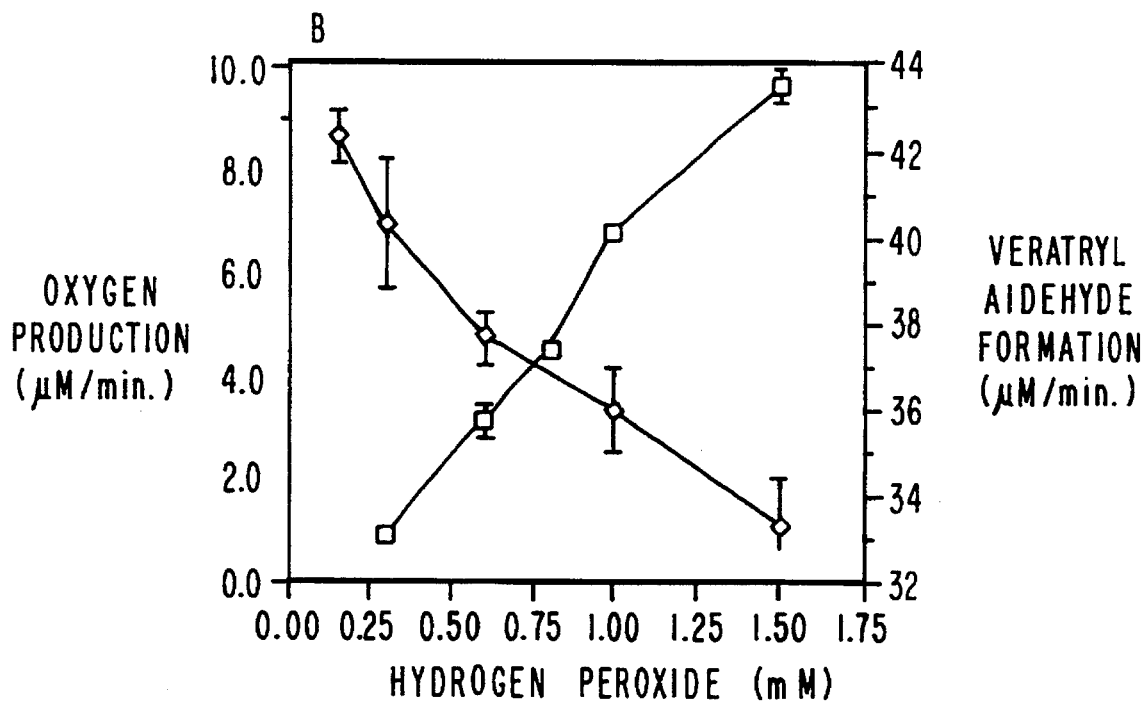

The effects of $H_2O_2$ on veratryl alcohol oxidation and the evolution of molecular oxygen are presented in FIGS. 8 and 9. The rate of $O_2$ evolution and the inhibition of veratryl alcohol oxidation appear to be inversely related with respect to the $H_2O_2$ concentration. FIG. 8 shows the effect of $H_2O_2$ concentrations between 0.125 and 40 mM on the rates of veratryl aldehyde formation and $O_2$ production. A more detailed study was performed using $H_2O_2$ concentrations between 0.125 and 1.5 mM and is presented in FIG. 9. It has been reported that high concentrations of $H_2O_2$ result in the inactivation of LiP. Wariishi, H. et al., *J. Biol Chem.*, 266:20694–99 (1991). To ensure that the inhibition of veratryl aldehyde formation (at $H_2O_2$ concentrations between 0.125 and 1.5 mM) was not due to the formation of an inactive form of LiPH2, the visible absorbance spectra of LiPH2 were examined in reaction mixtures containing 14.7 µM LiPH2 and the same ratios of $H_2O_2$/LiPH2 and veratryl alcohol/LiPH2 as were used in the previous experiment. The absorption spectra using a saturating concentration of veratryl alcohol indicated that LiPH2 was always in its activated state. For example, using 23 mM $H_2O_2$ and 72 mM veratryl alcohol (equivalent to 0.63 µM LiPH2, 1 mM $H_2O_2$ and 3 mM veratryl alcohol, FIGS. 6 and 7 the absorption maxima were at 528 and 554 nm. However, using lower concentrations of veratryl alcohol (23 mM $H_2O_2$ and only 575 µM veratryl alcohol) which was equivalent to 0.63 µM LiPH2, 1 mM $H_2O_2$, and 50 µM veratryl alcohol (FIGS. 6 and 7) the inactive form of LiPH2 was detected. The ability of other methoxybenzenes to mediate LiPH2-catalyzed $O_2$ production is shown in Table I.

TABLE I

Production of Molecular Oxygen by LiPH2 in the Presence of $H_2O_2$ using Various Electron Mediators

| Electron mediator | $E_{1/2}$ | Rate µM/min |
|---|---|---|
| Veratryl alcohol | NA | 6.7 ± 0.7 |
| Anisole (methoxybenzene) | 1.76 | ND |
| 1,2,3-Trimethoxybenzene | 1.42 | 4.8 ± 0.5 |
| 1,2,4-Trimethoxybenzene | 1.12 | 4.1 ± 0.5 |
| 1,2,4,5-Tetramethoxybenzene | 0.81 | ND |

TABLE I-continued

Production of Molecular Oxygen by LiPH2 in the Presence of $H_2O_2$ using Various Electron Mediators

| Electron mediator | $E_{1/2}$ | Rate µM/min |
|---|---|---|

The reaction mixtures contained 100 mM sodium acetate, pH 5.5, 0.8 µM LiPH2, 1 mM $H_2O_2$ and 3 mM electron mediator. The values for $E_{1/2}$ were obtained from reference 25.
(NA, not available; ND, not detectable.)

It was postulated that the evolution of oxygen was due to the one electron oxidation of $H_2O_2$ by the cation radical of veratryl alcohol to form superoxide ($O_2^-\cdot$) and its subsequent dismutation to yield $O_2$. Thus, it would be expected that superoxide dismutase would enhance the rate of $O_2$ evolution via this mechanism. When 98 units/ml superoxide dismutase was added to reaction mixtures containing LiPH2, $H_2O_2$, and veratryl alcohol, the rate of $O_2$ evolution was increased to 11.8 µM/min as compared with 4.1 µM/min in the absence of superoxide dismutase. The addition of boiled superoxide dismutase had no effect on the rate of $O_2$ evolution.

It has been previously reported that oxalate, which is produced by *P. chrysosporium*, can serve as an electron donor for the reduction of the veratryl alcohol cation radical. E.g., Akamatsu, Y. et al., *FEBS Lett.*, 269:261–63 (1990).

Figure 10:
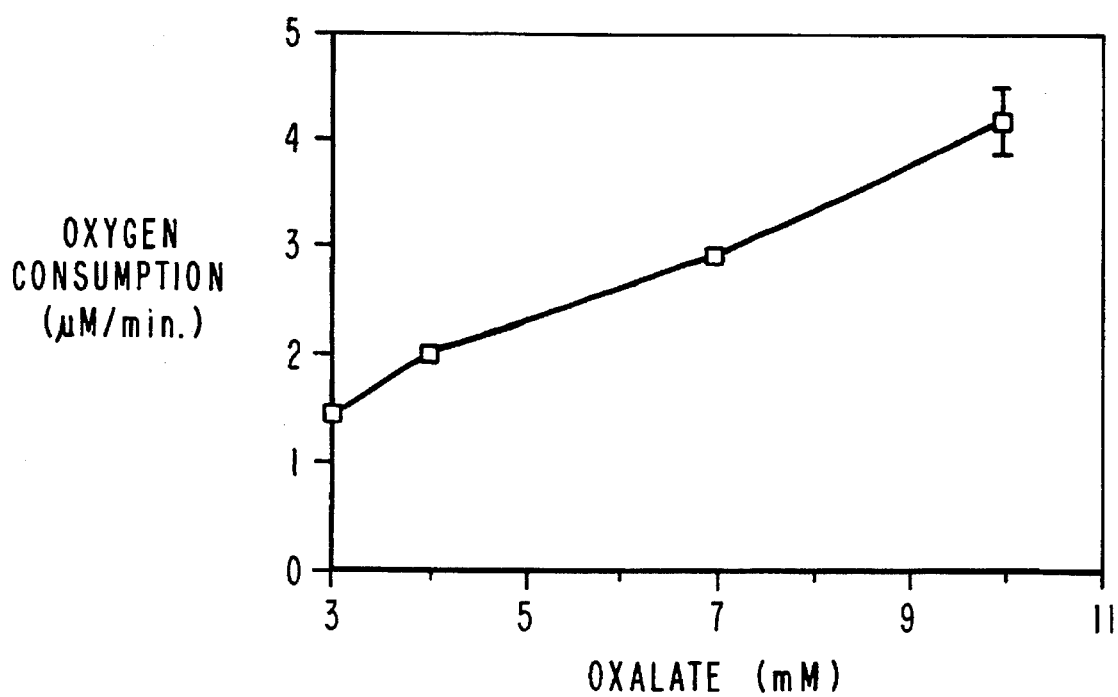
FIG. 10. Effect of oxalate on the rate of LiPH2-catalyzed oxygen consumption. The reaction mixtures contained 100 mM sodium acetate, pH 5.0, 0.63 µM LiPH2, 1 mM $H_2O_2$, 3 mM veratryl alcohol, and the indicated oxalate concentrations. The values represent the mean of triplicate measurements. The error bars indicate standard deviations.

The oxidation of oxalate by the veratryl alcohol cation radical produces the carbon dioxide anion radical ($CO_2$—). The carbon dioxide anion radical reduces molecular oxygen to $O_2$—. Thus, oxygen consumption was observed in reaction mixtures containing LiP, $H_2O_2$, veratryl alcohol, and oxalate. The effect of the oxalate concentration on $O_2$ consumption in reaction mixtures containing LiPH2, $H_2O_2$, and veratryl alcohol is shown in FIG. 10. It should be noted that some $O_2$ production is observed when no oxalate was added to the reaction mixture. Therefore, the zero point on the abscissa was left out of FIG. 10.

Figure 11:
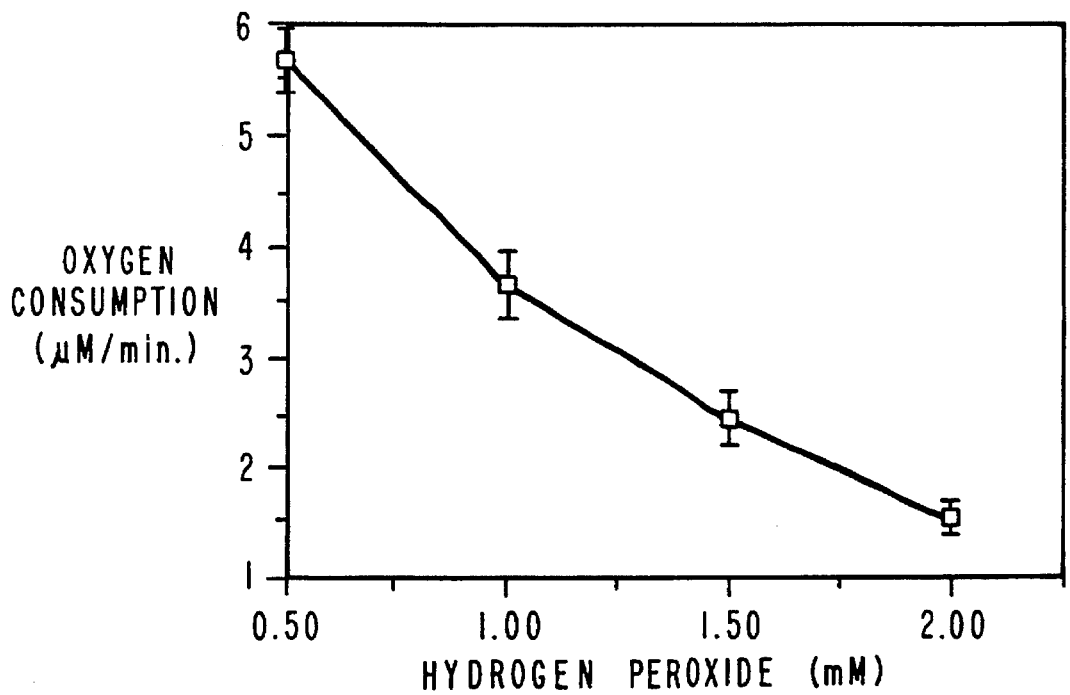
FIG. 11. Effect of hydrogen peroxide on the rate of LiPH2-catalyzed oxygen consumption. The reaction mixtures contained 100 mM sodium acetate, pH 5.0, 0.63 µM LiPH2, 3 mM veratryl alcohol, 10 mM oxalate, pH 5.0, and the indicated concentrations of $H_2O_2$. All values represent the mean of triplicate measurements. The standard deviations are indicated by the error bars.
Figure 12:
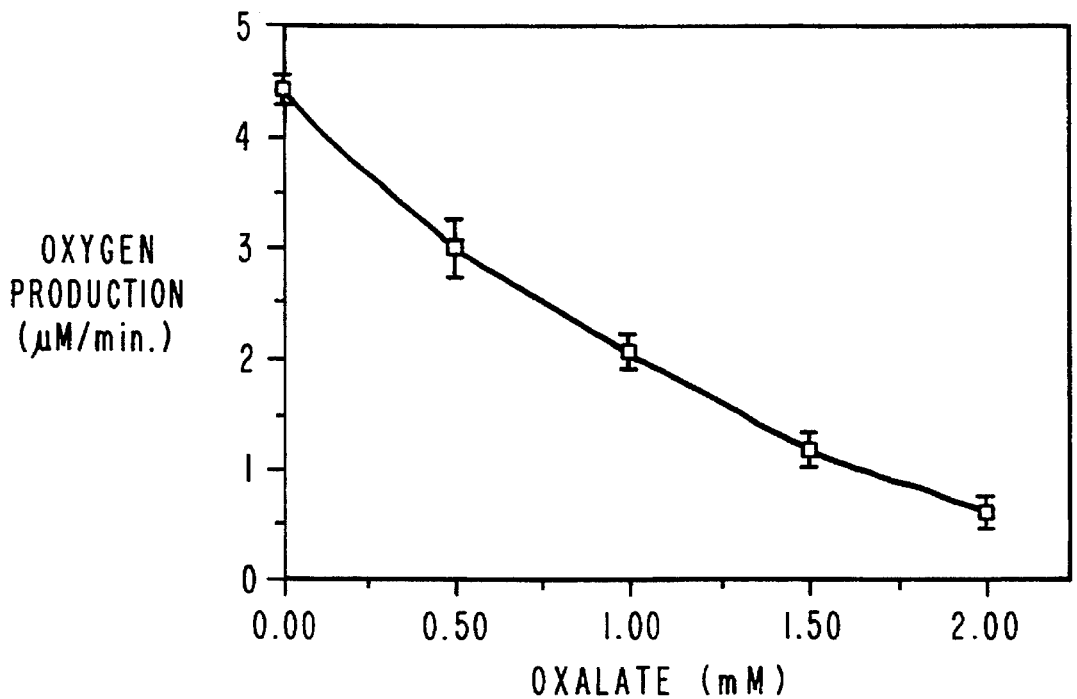
FIG. 12. Effect of oxalate on the rate of LiPH2-catalyzed oxygen production. The reaction mixtures contained 100 mM sodium acetate, pH 5.0, 0.63 µM LiPH2, 1 mM $H_2O_2$, 3 mM veratryl alcohol, and the indicated concentrations of oxalate. The values represent the mean of triplicate measurements. The error bars indicate standard deviation.

Since it appeared that $H_2O_2$ also reduced the veratryl alcohol cation radical to produce $O_2$— and subsequently $O_2$, it would be expected that higher $H_2O_2$ concentrations would inhibit $O_2$ consumption in reaction mixtures containing oxalate. FIG. 11 shows the effect of increasing the $H_2O_2$ concentration on the rate of $O_2$ consumption in reaction mixtures containing LiPH2, veratryl alcohol, and oxalate. Indeed, the rate of $O_2$ consumption decreased with increasing concentrations of $H_2O_2$. The effect of increasing oxalate concentration on the rate of LiPH2-catalyzed $O_2$ production is presented in FIG. 22. The rate of $O_2$ production was inhibited by increasing concentrations of oxalate.

The results of this investigation demonstrate that LiPH2 can catalyze the one electron oxidation of $H_2O_2$ using veratryl alcohol as an electron mediator. The $O_2$— produced by this reaction dismutates to $O_2$ and $H_2O_2$. Therefore, the net reaction catalyzed by LiPH2 is the production of $O_2$ from $H_2O_2$. This mechanism of $O_2$ production was further evidenced by the fact that superoxide dismutase stimulated the rate of $O_2$ evolution. The production of oxygen in the absence of veratryl alcohol might be due to reactions involving the inactive form of LiPH2. When catalytic amounts of veratryl alcohol (i.e., 50 µM) were added, the highest rate of $O_2$ production was obtained. This indicated that there were two mechanisms for $O_2$ production by LiPH2: one involving the inactive form of LiPH2 and one involving the veratryl alcohol cation radical.

Evidence for this arises from the fact that when the rate of $O_2$ production in the absence of veratryl alcohol (6.5 μM/min) was added to the $O_2$ production rate with saturating concentrations of veratryl alcohol (i,e., 3 mM veratryl alcohol gave 6.0 μM/min), a rate of 12.5 μM/min was obtained. The rate of $O_2$ production in the presence of a catalytic amount of veratryl alcohol (i.e. 50 μM gave 12.0 μM/min, about the sum of these two rates.

Veratryl aldehyde formation was inhibited by $H_2O_2$ apparently by the one electron reduction of the veratryl alcohol cation radical back to veratryl alcohol; not by inactivation of the enzyme. The visible absorbance spectrum of LiPH2 in this reaction mixture showed that the enzyme was in the compound II state. Therefore, the inhibition of veratryl aldehyde formation at concentrations of $H_2O_2$ between 0.125 mM and 1.5 mM ,was not due to the inactivation of LiP (i.e., formation of compound III). It was also found that other methoxybenzenes, which are often considered lignin model compounds, could serve as the electron mediator for LiPH2-catalyzed $O_2$ production. The ability of these methoxybenzenes to mediate LiP-catalyzed $O_2$ production was related to the redox potential of the methoxybenzene. The redox potential for the one electron oxidation of $H_2O_2$ to $O_2$— is 0.89 V. The redox potential of 1,2,4,5-tetramethoxybenzene is 0.81 V. Accordingly, no $O_2$ production was observed when 1,2,4,5-tetramethoxybenzene was used as the electron mediator. Although the redox potential of anisole (methoxybenzene) is sufficient to promote the oxidation of $H_2O_2$ (1.76 V), it is not a substrate for lignin peroxidase. Therefore, no $O_2$ production was observed in reaction mixtures containing anisole. The other methoxybenzenes have the appropriate redox potential for oxidation of $H_2O_2$ and $O_2$ evolution was observed when these were used with LiP and $H_2O_2$.

In an earlier study by Magnusson et al., *J. Biol. Chem.*, 259:197–205 (1984), $O_2$ evolution was observed following the oxidation of iodide to hypoiodite by thyroid peroxidase. It was concluded that $O_2$ evolution was due to the oxidation of $H_2O_2$ by hypoiodite. Studies from our laboratory show that $O_2$ is produced following the oxidation of iodide by LiPH2. The reaction of hypoiodite with $H_2O_2$ to produce molecular oxygen is considered to be a two-electron process. Shah, M. et al, *Oxidation of Halides by Peroxidases and Their Subsequent Reductions, Arch. Biochem. Biophys.*, 300:000 (January 1993). However, the veratryl alcohol-dependent $O_2$ production arises from the one-electron oxidation of $H_2O_2$ by the veratryl alcohol cation radical to produce $O_2$—. Other methoxybenzenes, which are substrates for LiP, also served as the electron mediator for $O_2$ production. These methoxybenzenes also form cation radicals when they are oxidized by LiP.

Other investigations have shown that electron donors such as oxalate and EDTA can reduce the veratryl alcohol cation radical back to veratryl alcohol. Studies by Akamatsu, Y. et al., *FEBS Lett.*, 269:261–63 (1990) demonstrated that oxalate was a noncompetitive inhibitor of LiP catalyzed veratryl alcohol oxidation. The $CO_2$— produced by the oxidation of oxalate has been shown to consume molecular oxygen.

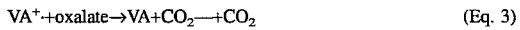

$$VA^+ + oxalate \rightarrow VA + CO_2{-} + CO_2 \qquad (Eq.\ 3)$$

$$CO_2{-} + O_2 \rightarrow CO_2 + O_2{-} \qquad (Eq.\ 4)$$

In the present study it was found that $O_2$ consumption by this mechanism could be inhibited by increasing concentrations of $H_2O_2$. The inhibition appears to be due to the competing reaction of $H_2O_2$ with the veratryl alcohol cation radical. It was also found that the rate of LiPH2-catalyzed $O_2$ production was inhibited by increasing concentrations of oxalate. Therefore, it was concluded that if oxalate donated an electron to the veratryl alcohol cation radical, oxygen consumption would result due to reactions 3 and 4. However, if $H_2O_2$ was the electron donor, the result was oxygen production via reactions 1 and 2. These results imply that the rates of $O_2$ production or $O_2$ consumption by LiPH2 are dependent on the relative concentrations of $H_2O_2$ and oxalate (or possibly other organic acids). The importance of the $O_2$ concentration in lignin degradation by *P. chrysosporium* has been demonstrated in previous studies. It was found that flushing cultures of *P. chrysosporium* with 100% $O_2$, as opposed to air, enhanced the rate of lignin degradation. Since *P. chrysosporium* produces $H_2O_2$, veratryl alcohol, and oxalate, the mechanisms described here may be involved in regulating the $O_2$ concentration for the degradation of lignin in wood by *P. chrysosporium*.

V. Summary

From the foregoing it should be understood that any number of oxidation and/or reduction reactions can be carried out depending upon the reaction conditions which are chosen. For example, the reaction mechanisms proposed by the present invention allow for the formation of superoxide, iodide, hydroxyl, organic acid, and hydroquinone radicals with greatly varying redox potentials. Depending upon the targeted substrate the raw materials added to the system can be optimized to yield the most efficient and sustainable reaction sequence.

Through the careful manipulation of the reactants and the reaction conditions, oxidations and reductions can be carried out in a far more predictable manner than heretofore possible. In addition, because many of the complex chemicals necessary to carry out the reactions can be derived from simple organisms, such as white rot fungi, the reactions are far more economically feasible than conventional oxidation and reduction reactions.

Finally, because the oxidation/reduction reactions of the present invention can easily be carried out on a large scale basis and are sustainable as long as there exist nutrient targeted substrates, they are especially well suited to remediate any number of toxic substances now found throughout the country in toxic waste sites or other remediation sites.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Patent is:

1. A method of selectively oxidizing or reducing a targeted substrate, the method including the steps of;

providing a peroxidase to serve as a free radical generating catalyst;

adding a suitable mediator which can be oxidized by said peroxidase to form the free radical of said mediator, whereby said free radical of said mediator is generated by a reaction between said peroxidase and said mediator, said free radical of said mediator being an oxidizing agent;

adding hydrogen peroxide which can be oxidized by said free radical of said mediator to form superoxide, whereby said superoxide is generated by a reaction between said free radical of said mediator and said hydrogen peroxide; and exposing at least one of said free radical of said mediator or said superoxide so generated to a targeted substrate, said substrate reacting in a oxidation/reduction reaction with at least one of said free radical of said mediator or said superoxide.

2. A method as defined in claim 1 wherein said targeted substrate is oxygen and said oxygen is reduced to superoxide.

3. A method as defined in claim 1 wherein said superoxide dismutates to form molecular oxygen.

4. A method as defined in claim 2 wherein said superoxide dismutates to form molecular oxygen.

5. A method as defined in claim 1 wherein the peroxidase is provided by a white rot fungus.

6. A method as defined in claim 1 wherein the mediator is provided by a white rot fungus.

7. A method as defined in claim 5 wherein the mediator is provided by a white rot fungus.

8. A method as defined in claim 1 wherein the hydrogen peroxide is provided by a white rot fungus.

9. A method as defined in claim 7 wherein the hydrogen peroxide is provided by a white rot fungus.

10. A method of producing molecular oxygen in an oxidation/reduction involving a white rot fungi, the method comprising the steps of:

providing a peroxidase to serve as a free radical generating catalyst;

adding a suitable mediator which can be oxidized by said peroxidase to form the free radical of said mediator, whereby said free radical of said mediator is generated by a reaction between said peroxidase and said mediator, said free radical of said mediator being an oxidizing agent;

adding hydrogen peroxide as a reductant which can be oxidized by said free radical of said mediator to form superoxide, whereby said superoxide is generated by a reaction between said free radical of said mediator and said hydrogen peroxide; and allowing said superoxide to dismutate into molecular oxygen and hydrogen peroxide.

11. A method for producing molecular oxygen comprising the steps of:

providing a peroxidase;

providing a mediator for reaction with said peroxidase; and providing hydrogen peroxide for reaction with the peroxidase in the presence of the mediator in order to produce molecular oxygen.

12. A method as defined in claim 11 wherein hydrogen peroxide is added in an amount sufficient to maintain the hydrogen peroxide concentration in the range of about 1 to about 50 mM.

13. A method as defined in claim 11 wherein hydrogen peroxide is added in an amount sufficient to maintain the hydrogen peroxide concentration in the range of about 5 to about 25 mM.

14. A method as defined in claim 11 wherein hydrogen peroxide is added in an amount sufficient to maintain the hydrogen peroxide concentration in the range of about 10 to about 20 mM.

* * * * *

UNITED STATES PATENT AND TRADEMARK OFFICE
CERTIFICATE OF CORRECTION

PATENT NO. : 5,468,628

DATED : November 21, 1995

INVENTOR(S) : STEVEN D. AUST, et al.

It is certified that error appears in the above-indentified patent and that said Letters Patent is hereby corrected as shown below:

Title page of patent, item [56], column 2, line 13 of text, "Degration" should be --Degradation--

Title page of patent, item [56], column 2, line 13 of text, "Enfironmental" should be --Environmental--

Title page, column 2, item [57], line 1 of text, after "methods" delete ";"

Title page, column 2, item [57], last line of Abstract, after "peroxide." insert the following, without paragraph structures:

The free radical generating catalyst is generally activated in the presence of hydrogen peroxide and reacts with the mediator to form the free radical of the mediator, which is an oxidant. The free radical of the mediator in turn reacts with the reductant to form the free radical of the reductant, which is also a reductant. The free radical oxidants and reductants can react directly with targeted substrates to carry out either oxidation or reduction reactions, or they can further react in other intermediate reactions to form additional oxidants and reductants. Targeted substrates include, but are not limited to, toxic waste materials, particularly chlorinated hydrocarbons such as DDT, CC14, TCDD, or PCBs.

Column 2, line 17, after "advantage" insert --of--

Column 2, line 19, delete "amount"

Column 2, line 38, "Tien, Met al.," should be --Tien, M. et al.,--

Column 4, line 20, "(or"mediator)" should be --(or "mediator")--

Column 6, line 49, "10 G, gain" should be --1.0 Gain,--

Column 6, line 50, "50 mW,," should be --50 mW,--

Column 6, line 67, "10 G" should be --1.0 G--

Column 7, line 1, "i OG" should be --1.0 G--

Column 13, line 51, after "noted" insert --that--

UNITED STATES PATENT AND TRADEMARK OFFICE
CERTIFICATE OF CORRECTION

PATENT NO.  : 5,468,628
DATED       : November 21, 1995
INVENTOR(S) : STEVEN D. AUST, et al.

It is certified that error appears in the above-indentified patent and that said Letters Patent is hereby corrected as shown below:

Column 14, line 7, "according the" should be --according to the--
Column 15, line 46, after "0.63 M" insert --)--
Column 15, line 47, "alcohol, FIGS. 6 and 7" should be --alcohol (FIGS. 6 and 7),--
Column 19, line 25, "off" should be --of:--

Signed and Sealed this

Fifteenth Day of April, 1997

Attest:

BRUCE LEHMAN

Attesting Officer    Commissioner of Patents and Trademarks